United States Patent
Dorshow et al.

(10) Patent No.: US 11,285,223 B2
(45) Date of Patent: *Mar. 29, 2022

(54) COMPOSITIONS AND METHODS FOR ASSESSING GUT FUNCTION

(71) Applicant: MediBeacon Inc., St. Louis, MO (US)

(72) Inventors: Richard B. Dorshow, St. Louis, MO (US); Steven J. Hanley, Wildwood, MO (US); Phillip I. Tarr, Clayton, MO (US)

(73) Assignee: MediBeacon Inc., St. Louis, MO (US)

( * ) Notice: Subject to any disclaimer, the term of this patent is extended or adjusted under 35 U.S.C. 154(b) by 87 days.

This patent is subject to a terminal disclaimer.

(21) Appl. No.: 16/200,311

(22) Filed: Nov. 26, 2018

(65) Prior Publication Data
US 2019/0091348 A1 Mar. 28, 2019

Related U.S. Application Data

(62) Division of application No. 14/538,770, filed on Nov. 11, 2014, now Pat. No. 11,077,211.

(60) Provisional application No. 61/902,637, filed on Nov. 11, 2013.

(51) Int. Cl.
*A61K 49/00* (2006.01)

(52) U.S. Cl.
CPC ...... *A61K 49/0052* (2013.01); *A61K 49/0021* (2013.01)

(58) Field of Classification Search
CPC .................. A61K 49/0021; A61K 49/0052
See application file for complete search history.

(56) References Cited

U.S. PATENT DOCUMENTS

| | | | |
|---|---|---|---|
| 9,632,094 B2 * | 4/2017 | Gretz | A61B 5/68335 |
| 2003/0236452 A1 | 12/2003 | Melker et al. | |
| 2006/0095102 A1 | 5/2006 | Perez | |
| 2008/0281173 A1 | 11/2008 | Esenaliev et al. | |
| 2008/0299038 A1 * | 12/2008 | Rajagopalan | A61K 49/0013 424/1.65 |
| 2009/0198053 A1 | 8/2009 | Rajagopalan et al. | |
| 2011/0017217 A1 | 1/2011 | Wood et al. | |
| 2011/0065771 A1 | 3/2011 | Colgan et al. | |
| 2011/0250140 A1 | 10/2011 | Poreddy et al. | |
| 2012/0027682 A1 | 2/2012 | Neumann et al. | |
| 2013/0101513 A1 * | 4/2013 | Yang | A61B 5/0059 424/9.1 |
| 2013/0116512 A1 | 5/2013 | Imran | |
| 2013/0211195 A1 | 8/2013 | Yao et al. | |
| 2013/0211215 A1 | 8/2013 | Heglund et al. | |
| 2013/0216482 A1 | 8/2013 | Kwon et al. | |
| 2015/0011542 A1 * | 1/2015 | Boelsterli | A61K 31/4704 514/232.8 |
| 2015/0306486 A1 | 10/2015 | Logan et al. | |
| 2017/0298030 A9 | 10/2017 | Rajagopalan et al. | |

FOREIGN PATENT DOCUMENTS

| | | |
|---|---|---|
| JP | 2011173859 A | 9/2011 |
| WO | 2007002332 A2 | 1/2007 |
| WO | 2007149479 A1 | 12/2007 |
| WO | 2009018405 A1 | 2/2009 |
| WO | 2010078025 A1 | 7/2010 |

OTHER PUBLICATIONS

Xu et al., Journal of Pediatric Gastroenterology & Nutrition, 1996, 23(4), p. 430-437. (Year: 1996).*
Vasquez et al., PLOS One, 2011, 6(6), p. 1-12. (Year: 2011).*
Morin , Poster 143, 6th European Molecular Imaging Meeting—EMIM 2011. (Year: 2011).*
Adsorption, https://en.wikipedia.org/wiki/Adsorption, Sep. 8, 2020. (Year: 2020).*
Wheeler et al., Clin Sci Mol Med, 1978, 54(5), p. 495-501 (abstract). (Year: 1978).*
Wheeler et al., Clin Sci Mol Med, 1978, 54(5), p. 495-501. (Year: 1978).*
Miele et al., "Altered Intestinal Premeability is Predictive of Early Relapse in Children with Steroid-Responsive Ulcerative Colitis", Alimentary Pharmacology & Therapeutics, 2007, vol. 225, pp. 933-939.
Oriishi et al., "Evaluation of Intestinal Premeability in Patients with Inflammatory Bowel Disease Using Lactulose and Measuring Antibodies to Lipid A", Second Department of Medicine, Kurume University School of Medicine, 1995, vol. 36, pp. 891-896.
Pearson et al., "Intestinal Premeability in Children with Crohn's Disease and Coeliac Disease", British Medical Journal, Jul. 3, 1982, vol. 285, pp. 20-21.
Poreddy et al. "Exogenous fluorescent tracer agents based on pegylated pyrazine dyes for real-time point-of-care measurement of glomerular filtration rate", Bioorganic & Medicinal Chemistry, Mar. 10, 2012, vol. 20, No. 8, pp. 2490-2497.
Rajagopalan et al., "Hydrophilic Pyrazine Dyes as Exogenous Fluorescent Tracer Agents for Real-Time Point-of-Care Measurement of Glomerular Filtration Rate", J. Med. Chem, 2011, vol. 54, pp. 5048-5058.
Shirai et al., "Syntheses and Fluorescent Properties of 2,5-Diamino-3,6-dicyanopyrazine Dyes", Dyes and Pigments, 1998, vol. 39, No. 1, pp. 49-68.
Szabo et al., "In Vivo Fluorescence Microscopic Imaging for Dynamic Quantitative Assessment of Intestinal Mucosa Permeability in Mice", Journal of Surgical Research, Apr. 2008, vol. 145, No. 2, pp. 179-185.
Wei et al., "Fatty Acid Synthase Modulates Intestinal Barrier Function through Palmitoylation of Mucin 2", Cell Host & Microbe., Feb. 16, 2012, vol. 11, No. 2, pp. 140-152.

(Continued)

*Primary Examiner* — Michael G. Hartley
*Assistant Examiner* — Leah H Schlientz
(74) *Attorney, Agent, or Firm* — Armstrong Teasdale LLP

(57) ABSTRACT

Compositions and methods for assessing gut function are disclosed. They are designed to provide accurate, rapid, point-of-care or in-community assessment of enteric dysfunction.

9 Claims, 8 Drawing Sheets

(56) References Cited

OTHER PUBLICATIONS

Wild et al., "The Mechanisms of Prednisone Inhibition of Inflammation in Crohn's Disease Involve Changes in Intestinal Premeability, Mucosal TNF Production and Nuclear Factor kappa B Expression", Aliment Pharmacol Ther, 2003, vol. 18, pp. 309-317.
EPO Extended European Search Report, EP 14859902.0-1466/3068399 dated May 11, 2017, 7 pages.
International Search Report and Written Opinion, PCT Application No. PCT/US14/65233 dated Mar. 27, 2015, 20 pages.
Kiesslich et al., "Local barrier dysfunction identified by confocal laser endomicroscopy predicts relapse in inflammatory bowel disease", Gut, 1012, pp. 1146-1153.
Söderholm et al., "Epithelial Permeability to Proteins in the Noninflamed Ileum of Crohn's Disease?", Gastroenterology, 1999, vol. 117, pp. 65-72.
Kimura et al., "Drug absorption from large intestine: physicochemical factors governing drug absorption", Biological and Pharmaceutical Bulletin, Feb. 1994, vol. 17, No. 2, pp. 327-333.
Brenner et al., "Quantitative Importance of Changes in Postglomerular Colloid Osmotic Pressure in Mediating Glomerulotubular Balance in the Rat," The Journal of Clinical Investigation, vol. 52, (1973), pp. 190-197.
Chinen et al., "Fluorescence-Enhanced Europium-Diethylenetriaminepentaacetic (DTPA)-Monoamide Complexes for the Assessment of Renal Function," J. Med. Chem., vol. 51, (2008), pp. 957-962.
Dean et al., "Inulin, Diodone, Creatinine And Urea Clearances In Newborn Infants," J. Physiol., vol. 106, (1947), pp. 431-439.
Debreczeny et al., "Transdermal Optical Renal Function Monitoring in Humans: Development, Verification, and Validation of a Prototype Device," Journal of Biomedical Optics, vol. 23, No. 5, (May 2018), 057003-1-057003-9.
Friedman et al., "A comparison of the renal clearances of allantoin and inulin in man," Fed. Proc., vol. 7, No. 1 Pt 1, (1948), 1 page.
Gregory et al., "Studies on Hypertension; Effect of Lowering the Blood Pressures of Hypertensive Patients by High Spinal Anesthesia on the Renal Function as Measured by Inulin and Diodrast Clearances," Arch. Intern. Med. (Chic), vol. 77, (1946), pp. 385-392.
Levin et al., "The Effect of Chronic Anemia on Renal Function as Measured by Inulin and Diodrast Clearances," Proc. Annu. Meet. Cent. Soc. Clin. Res. U. S., vol. 20, (1947), 3 pages.

Nagpal et al., "Combined Fluorescein, Indocyanine angiography and Optical Coherent Tomography Using Spectralis," Rajasthan Journal of Ophthalmology, (2011), 8 pages.
Navar et al., "Distal Tubular Feedback in the Autoregulation of Single Nephron Glomerular Filtration Rate," J. Clin. Invest., vol. 53, (1974), pp. 516-525.
Nicholson et al., "Renal Function as Affected by Experimental Unilateral Kidney Lesions : I. Nephrosis Due to Sodium Rartrate," J. Exp. Med., Vil 68, (1938), pp. 439-456.
Pill et al., "Fluorescein-labeled Sinistrin as Marker of Glomerular Filtration Rate," European Journal of Medicinal Chemistry, vol. 40, (2005), pp. 1056-1061.
Poujeol et al., "Glomerular Filtration Rate and Microsphere Distributions in Single Nephron of Rat Kidney," Pflugers Arch., vol. 357, (1975), pp. 291-301.
Robson et al., "The Determination of the Renal Clearance of Inulin in Man," Q. J. Exp. Physiol., vol. 35, (1949), pp. 111-134.
Schock-Kusch et al., "Transcutaneous measurement of glomerular filtration rate using FITC-sinistrin in rats," Nephrol Dial Transplant, vol. 24, (2009), pp. 2997-3001.
Shannon et al., "The Renal Excretion of Inulin and Creatinine by the Anaesthetized Dog and the Pump-Lung-Kidney Preparation", J. Physiol., vol. 98, (1940), pp. 97-108.
Yu et al., "Rapid determination of renal filtration function using an optical ratiometric imaging approach," Am. J. Physiol. Renal. Physiol., vol. 292, (2007), pp. F1873-F1880.
International Search Report received for PCT Patent Application No. PCT/US2019/013784, dated May 7, 2019, 6 pages.
International Preliminary Report on Patentability received for PCT Patent Application No. PCT/US2019/013784, dated Jul. 30, 2020, 8 pages.
Costantini et al., "Quantitative Assessment of Intestinal Injury Using a Novel In Vivo, Near-infrared Imaging Technique", Molecular Imaging, Jan./Feb. 2010, vol. 9, No. 1, pp. 30-39.
Krimsky et al., "Assessment of Intestinal Permeability in Rats by Permeation of Inulin-Fluorescein", J. Basic & Clinical Physiology & Pharmacology, 2000, vol. 11, No. 2, pp. 143-153.
Ma et al., "Is the small intestinal epithelium truly "tight" to inulin permeation?", Am. J. Physiol., 1991, vol. 260 (5 Pt 1), pp. G669-G676.
Sahoo et al., "Synthesis of novel coumarin derivatives and its biological evaluations", European Journal of Experimental Biology, 2012, vol. 2, No. 4, pp. 899-908.

* cited by examiner

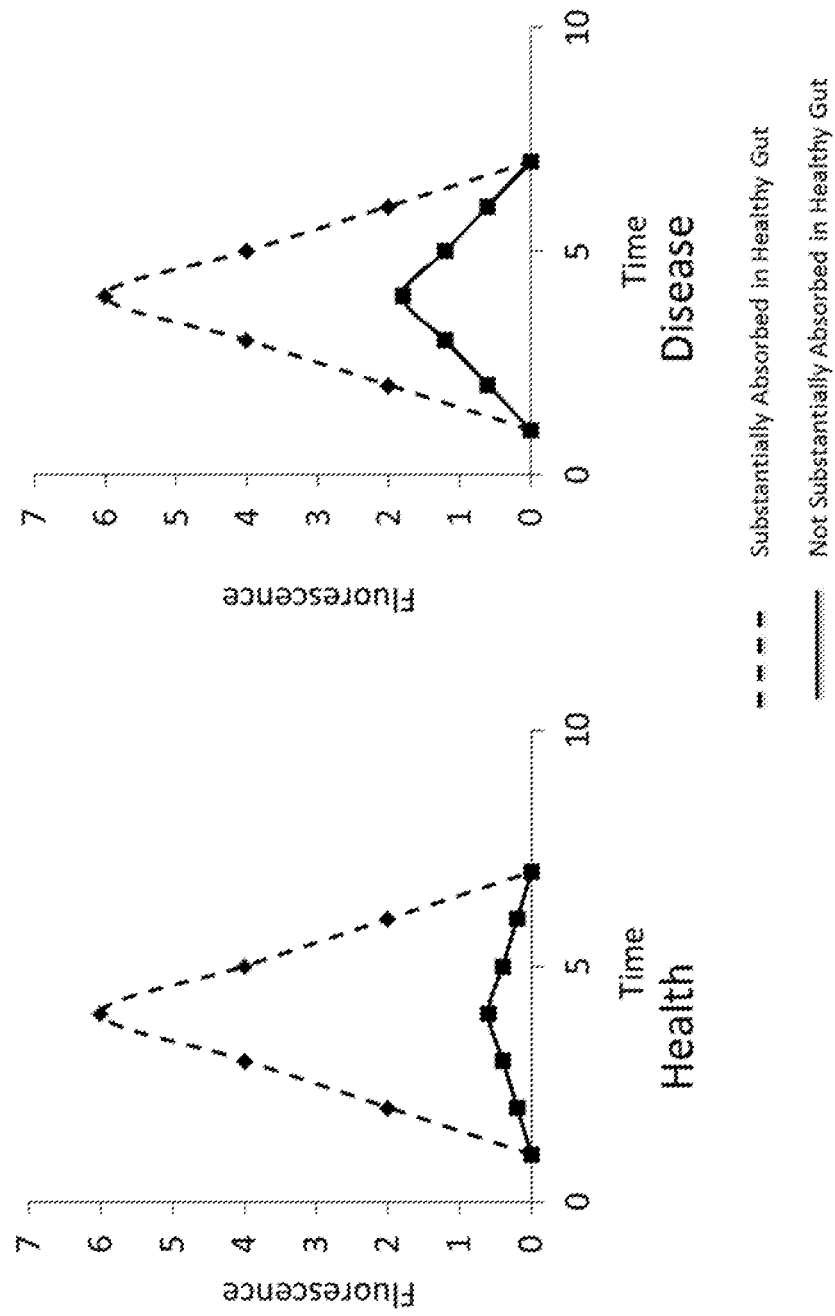

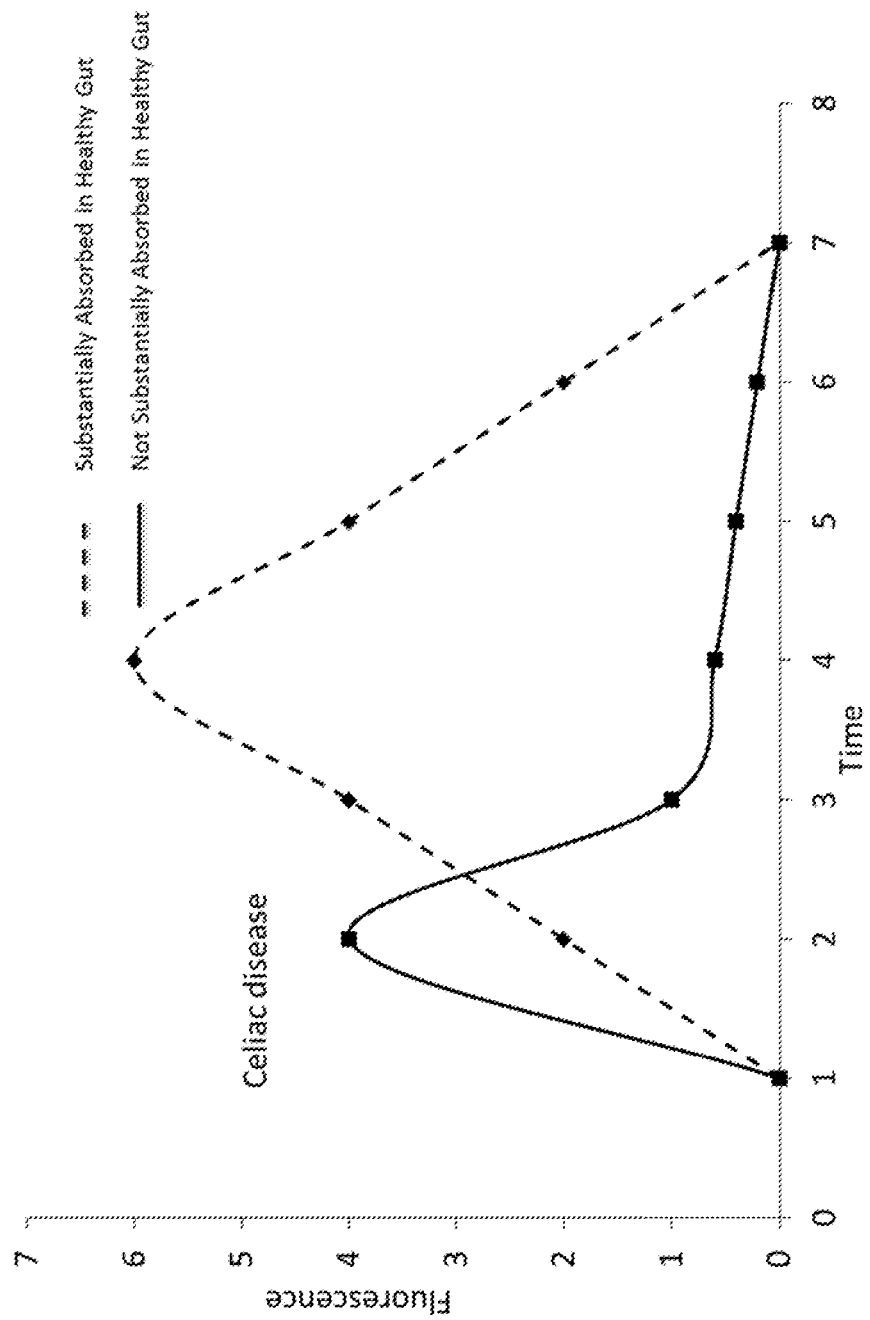

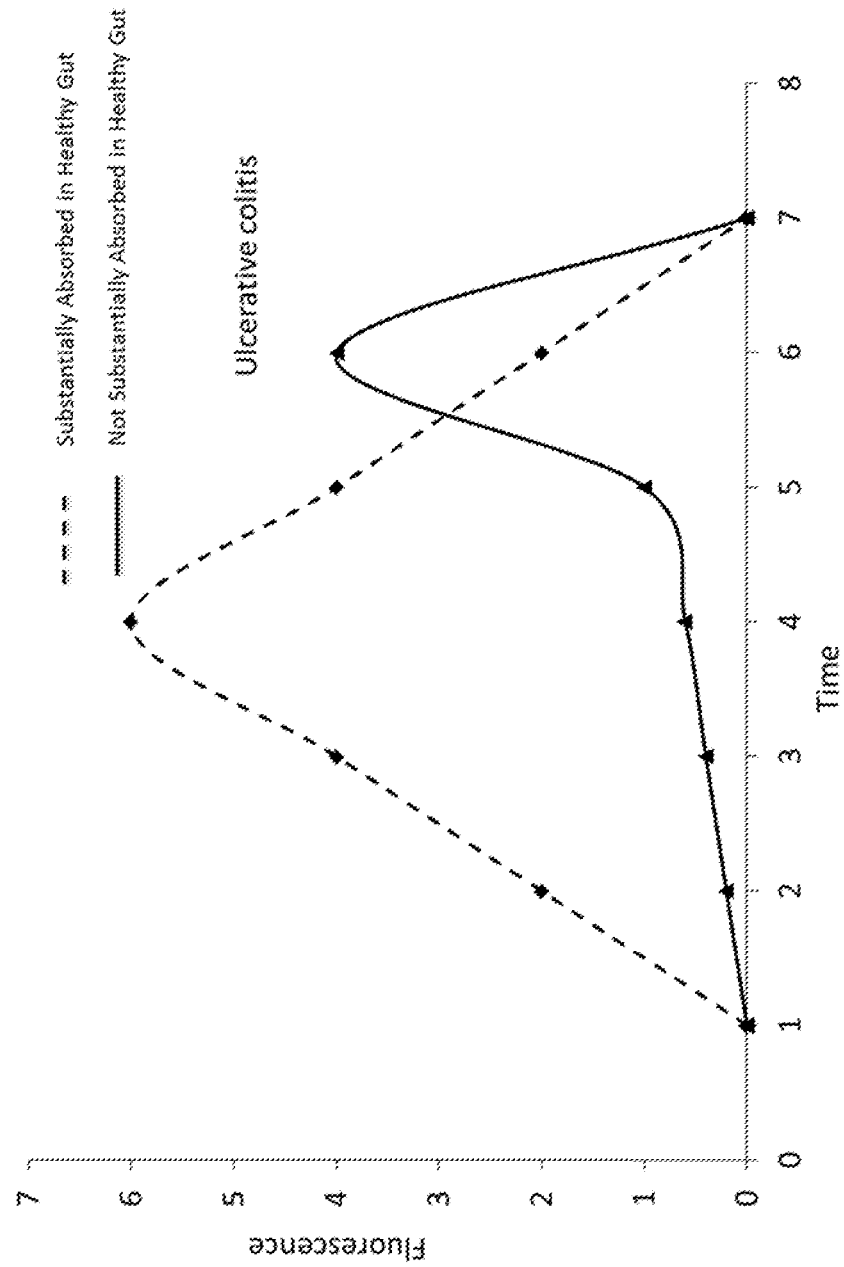

COMPOSITIONS AND METHODS FOR ASSESSING GUT FUNCTION

CROSS REFERENCE TO RELATED APPLICATIONS

This application is a divisional application of U.S. application Ser. No. 14/538,770 filed on Nov. 11, 2014, which claims the benefit of U.S. Provisional Application No. 61/902,637, entitled "Compositions and Methods for Assessing Gut Function," filed on Nov. 11, 2013, the contents of both are hereby incorporated by reference.

BACKGROUND

Field

The present disclosure relates to compositions and methods for assessing gut function, more specifically to noninvasive methods for assessing gut barrier function.

Related Art

Gut mucosal integrity is a major challenge facing clinical medicine. Proper functioning of the intestines depend on the mucosa having sufficient surface capacity with which to absorb nutrients as well has having sufficient structural integrity to maintain the barrier function of the lining of this organ.

Abnormally increased gut permeability quite likely plays a role in inflammatory bowel diseases (IBD) (i.e., Crohn's disease and ulcerative colitis) and identifying abnormally increased gut permeability can be very helpful in diagnosing disease, as well as monitoring and adjusting therapy directed against gut inflammation. Identifying increased gut permeability might assist in the management of a variety of disorders that are not directly manifest as intestinal dysfunction. These disorders non-alcoholic fatty liver disease, cirrhosis of the liver, arthritis, diabetes, and irritable bowel syndrome.

Various molecular strategies to probe the structure and function of the small bowel have been developed. The chief goal of all of these strategies is to directly or indirectly assess the structural integrity of the intestinal epithelium, which is comprised of a carpet of highly specialized columnar epithelial cells joined by tight junctions and adherens junctions. Molecules are selected to probe the competency of uptake and of permeability. Generally, integrity lesions that result in increased passive diffusion across the mucosa are detected by challenging a host with a substance that is not found in the diet, and assessing its uptake and/or clearance by studying the blood and the urine. In this model, uptake and excretion are abnormal. Conversely, gut transport capacity is assessed by administering a challenge substance that is easily absorbed in health and disease, but where uptake is limited by surface availability (as would be hindered in anatomic short gut or diminished villous surface area). Such substances are then measured in the urine and blood, and uptake reflects a gut of appropriate mass.

The most widely used test is termed the lactulose to mannitol ratio (L:M). Sugars (i.e., lactulose and mannitol) are administered orally, and their excretion is measured in the urine. The basis for the test lies in their two differential molecular weights. The larger sugar, lactulose, MW=342, is minimally absorbed during transit through an intact gut lined by intact epithelial, with highly competent tight junction functionality, and this disaccharide is therefore considered nearly impermeant. The smaller sugar, mannitol (MW=182), in contrast, is assimilated by an intact as well as an injured (permeant) gut via transcellular pathways and this absorption is proportional to the absorptive capacity of the gut. Both sugars distribute throughout the body in a hydrophilic compartments, and are then cleared by glomerular filtration. They are then measured in tandem in the urine. The co-administration, and the use of ratios in the urine, obviate single molecule assessments, because the ratio is independent of gastric emptying, or partial vomiting of the challenge sugars. Other sugars have been used to measure small and large bowel permeability, and include rhamnose and sucralose and D-xylose.

Measurements of challenge substances can be technically difficult. If peak or repeated circulating values are sought, phlebotomy is required, and there are assumptions about the kinetics of the peak. A urine collection is less invasive, but usually occurs over multiple hours, and is cumbersome to perform. An indirect test, such as measuring bacterial metabolism reflecting undigested sugar, requires specialized equipment. Hence, specimen acquisition, handling, and analysis are all very critical, but difficult to perform.

Thus, there remains a need for improved methods and compositions for assessing gut function.

SUMMARY

Accordingly, the inventors herein disclose new compositions and methods for assessing gut function. The methods are designed to be noninvasive, sensitive, and convenient.

Provided is a composition for assessing gut function, and most specifically barrier integrity, in a subject in need thereof, comprising a fluorescent challenge molecule, wherein the fluorescent challenge molecule is not substantially absorbed by a healthy gut.

Provided is a composition for assessing gut function in a subject in need thereof, comprising at least two fluorescent challenge molecules, wherein one fluorescent challenge molecule is not substantially absorbed by a healthy gut, and the other is substantially absorbed by a healthy gut. The second molecule may possess different photophysical properties from the first challenge molecule. Thus, the two molecules display different absorption and emission wavelengths, and allow real-time measurement of uptake and permeability in the gut.

Provided is a method for assessing gut function in a subject in need thereof, comprising the steps of: administering an effective amount of a composition of a fluorescent challenge molecule, wherein the fluorescent challenge molecule is not substantially absorbed by a healthy gut into the subject's gut; irradiating the composition absorbed by the subject's gut with non-ionizing radiation, wherein the radiation causes the composition to fluoresce; detecting the fluorescence of the composition; and assessing gut function in the subject based on the detected fluorescence.

Provided is a method for assessing gut function in a subject in need thereof, comprising the steps of: administering an effective amount of a composition comprising two fluorescent challenge molecules—a fluorescent challenge molecule that is not substantially absorbed by a healthy gut, and a second fluorescent challenge molecule is substantially absorbed by a healthy gut—into the subject's gut; irradiating the composition absorbed by the subject's gut with non-ionizing radiation, wherein the radiation causes the composition to fluoresce; detecting the fluorescence of each fluorescent challenge molecule in the composition; and assessing gut function in the subject based on the detected fluorescence. GUT function is assessed by comparing the detected fluorescence of the fluorescent challenge molecule that is not substantially absorbed by a healthy gut to the fluorescent challenge molecule that is substantially absorbed by a healthy gut. The two fluorescent challenge molecules may possess different photophysical properties allowing for the simultaneous measurement of the fluorescence the two molecules.

Provided is a kit for assessing gut function in a subject in need thereof, comprising: a composition comprising one or more orally administered fluorescent challenge molecules, wherein the fluorescent challenge molecule(s) is not substantially absorbed by a healthy gut, and written instructions for assessing gut function in the subject, comprising the steps of: administering an effective amount of the composition into the subject's gut; irradiating the composition absorbed by the subject's gut with non-ionizing radiation, wherein the radiation causes the composition to fluoresce; detecting the fluorescence of the composition; and assessing gut function in the subject based on the detected fluorescence.

BRIEF DESCRIPTION OF THE DRAWINGS

FIG. 6 shows anticipated Fluorescence vs. Time Curves for compositions comprising both challenge molecules that are substantially and not substantially absorbed in healthy guts and diseased guts;

FIG. 7 shows an anticipated Fluorescence vs. Time Curve for compositions comprising both challenge molecules that are substantially and not substantially absorbed in a gut having a proximal injury; and FIG. 8 shows an anticipated Fluorescence vs. Time Curve for compositions comprising both challenge molecules that are substantially and not substantially absorbed in a gut having a distal injury.

DETAILED DESCRIPTION

Abbreviations and Definitions

Figure 1:
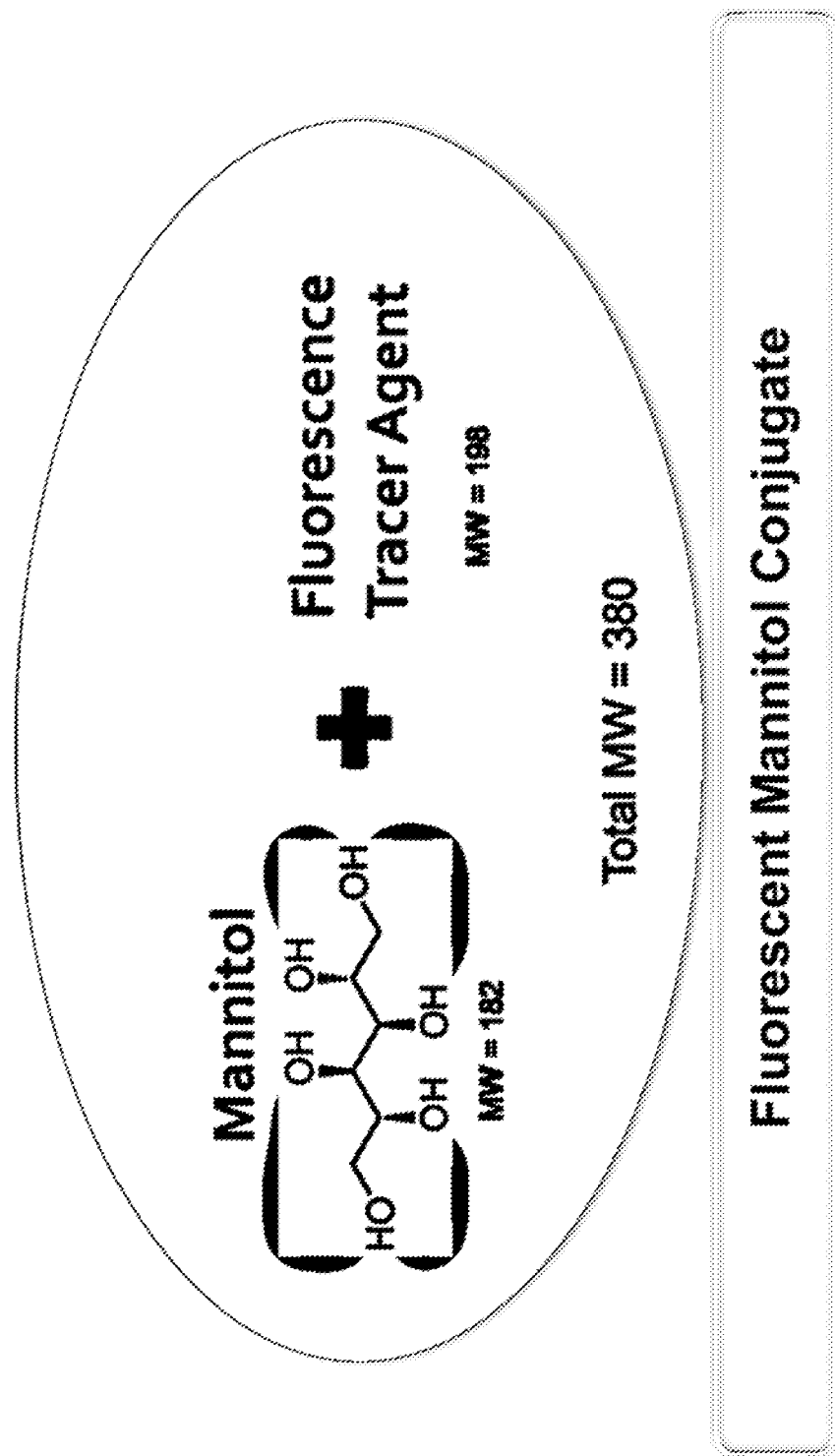
FIG. 1 shows an embodiment of a fluorescent challenge molecule, wherein the fluorescent dye is conjugated to mannitol.
Figure 2:
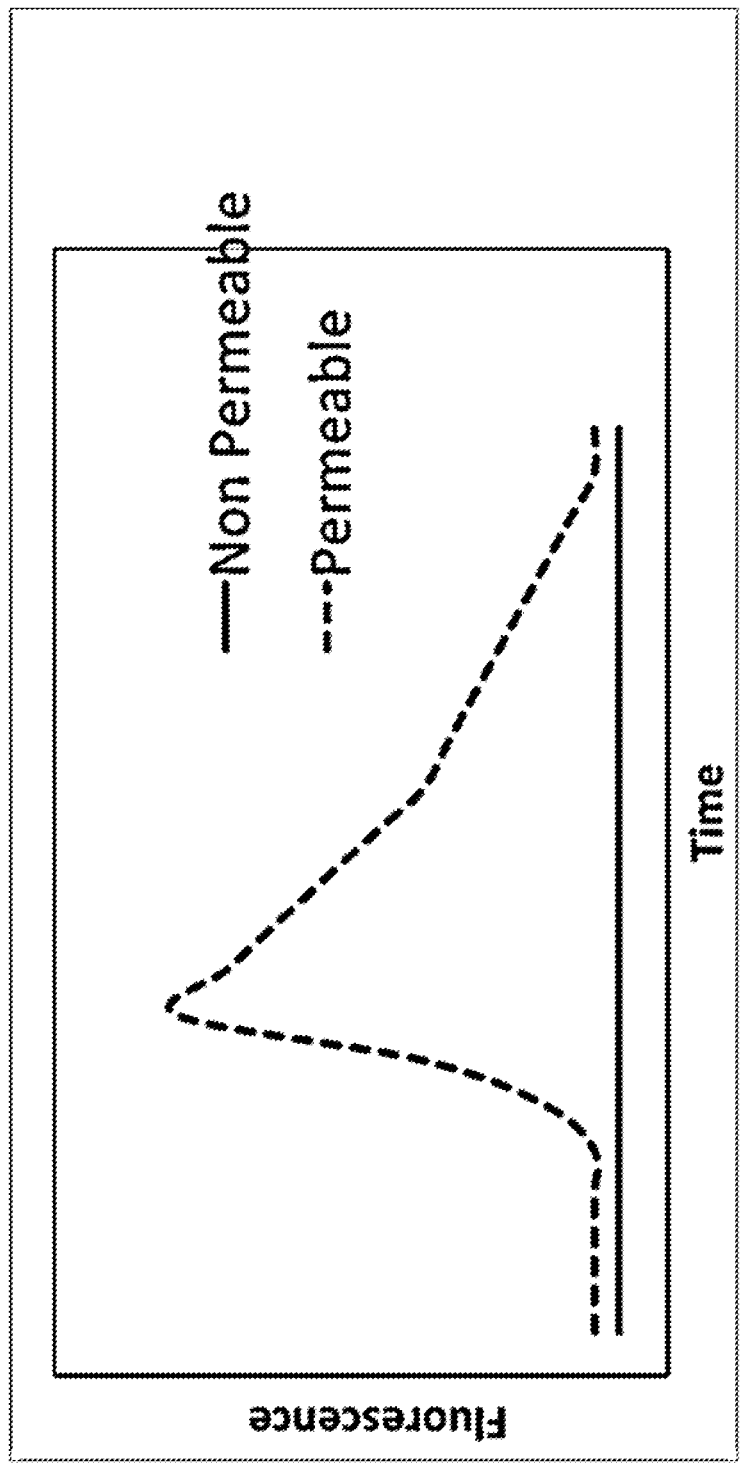
FIG. 2 shows anticipated fluorescence measurement data for permeable and non-permeable fluorescent challenge molecules administered to a subject.

To facilitate understanding of the disclosure, a number of terms and abbreviations as used herein are defined below as follows:

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

The term "about," as used herein when referring to a measurable value such as an amount of a compound, dose, time, temperature, and the like, is meant to encompass variations of 20%, 10%, 5%, 1%, 0.5%, or even 0.1% of the specified amount.

The term "gut" as used herein designates the gastrointestinal or digestive tract (also referred to as the alimentary canal) and it refers to the system of organs within multicellular animals which takes in food, digests it to extract energy and nutrients, and expels the remaining waste.

The term "gut function" as used herein refers to any aspect of the functioning of the gut and/or structural integrity of the gut. For example, the methods of the present disclosure may be used to provide an indication or assessment of: the absorptive capacity of the gut; the ability of the gut to absorb nutrients; the permeability of the gut; the ability of the gut to hydrolyze compounds; the surface area of the gut and/or small intestine; the functional surface area of the gut and/or small intestine; the barrier function of the gut; damage to the gut; the degree of mucosal damage in the gut; damage to the villi in, rater alia, the small intestine; the villous height of the brush border of the small intestine; the presence of any disease or pathology which is associated with a change in gut function as described herein; the presence of an inflammatory condition; the presence of a infection; the response to treatments to correct any or all of the above lesions, as well as any other aspect of gut functioning or gut structural integrity that would be evident to one of skill in the art.

The term "fluorescent dye" as used herein refers to a dye that absorbs light at a first wavelength and emits at second wavelength that is longer than the first wavelength.

The term "fluorescence" refers to luminescence in which the molecular absorption of a photon triggers the emission of another photon with a longer wavelength.

The term "challenge molecule" refers to a compound to be administered to a subject to observe the physiological response that occurs. The "challenge" may be, for example, introducing a compound to a subject to assess the gut. This may be one that is not normally absorbed by a healthy gut, wherein absorption may represent permeability of the gut.

The terms "degradation" and "digestion" as used herein refer to the chemical breakdown of a compound to release e.g. its component atoms or a simpler compound.

The term "carbohydrate" as used herein is defined to include polyhydroxy aldehydes, or polyhydroxy ketones or substances that yield such compounds on hydrolysis. The term "carbohydrate" includes monosaccharides, oligosaccharides, disaccharides, trisaccharides, tetrasaccharides, pentasaccharides, hexasaccharides, polysaccharides, homopolysaccharides, and heteropolysaccharides. The term includes any of the aldoses, as well as glucose, dextrose, mannose, galactose arabinose, xylose, ribose, fructose, sucrose, altrose, allose, idose, gulose, talose, lyxose, threose, erythrose, apiose, and any of the same in acid form. The term also includes deoxy sugars and deoxy-aldoses, including rhamnose and fucose. The term further includes glyceraldehyde, cellulose, starch, glycogen, and amylose. The term also includes carbohydrate derivatives, such as acetals, ketals, acyl esters and the like.

The term "non-ionizing radiation" refers to lower-energy radiation, such as visible light, near infrared, infrared, microwaves, and radio waves. The ability of an electromagnetic wave (photons) to ionize an atom or molecule depends on its frequency. Radiation on the short-wavelength end of the electromagnetic spectrum—x-rays, and gamma rays—is ionizing. Therefore, when using the term "non-ionizing radiation" it is intended to mean electromagnetic waves having a frequency not sufficient to ionize an atom or molecule.

The phrase "not substantially absorbed" is intended to refer to molecules that may be distinguished by the difference in their gut absorption in a healthy versus a diseased or injured gut. In certain embodiments, not substantially absorbed means less than 99% of the administered amount is absorbed. In certain embodiments, not substantially absorbed means less than 95% of the administered amount is absorbed. In certain embodiments, not substantially absorbed means less than 90% of the administered amount is absorbed. In certain embodiments, not substantially absorbed means less than 80% of the administered amount is absorbed. In certain embodiments, not substantially absorbed means less than 70% of the administered amount is absorbed. In certain embodiments, not substantially absorbed means less than 60% of the administered amount is absorbed. In certain embodiments, not substantially absorbed means less than 50% of the administered amount is absorbed. In certain embodiments, not substantially absorbed means less than 40% of the administered amount is absorbed. In certain embodiments, not substantially absorbed means less than 30% of the administered amount is absorbed. In certain embodiments, not substantially absorbed means less than 20% of the administered amount is absorbed. In certain embodiments, not substantially absorbed means less than 10% of the administered amount is absorbed. In certain embodiments, not substantially absorbed means less than 5% of the administered amount is absorbed. In certain embodiments, not substantially absorbed means less than 1% of the administered amount is absorbed. The phrase "not substantially absorbed," when describing compositions, methods and kits comprising more than one fluorescent challenge molecule, refers to combinations of challenge molecules that may be distinguished by the difference in their gut absorption in a healthy versus a diseased or injured gut. In certain embodiments, the ratio of each challenge molecule's gut absorbance is greater than about 1. In certain embodiments, the ratio of each challenge molecule's gut absorbance is greater than about 2. In certain embodiments, the ratio of each challenge molecule's gut absorbance is greater than about 3. In certain embodiments, the ratio of each challenge molecule's gut absorbance is greater than about 4. In certain embodiments, the ratio of each challenge molecule's gut absorbance is greater than about 5. In certain embodiments, the ratio of each challenge molecule's gut absorbance is greater than about 10. In certain embodiments, the ratio of each challenge molecule's gut absorbance is greater than about 20. In certain embodiments, the ratio of each challenge molecule's gut absorbance is greater than about 30. In certain embodiments, the ratio of each challenge molecule's gut absorbance is greater than about 40. In certain embodiments, the ratio of each challenge molecule's gut absorbance is greater than about 50.

The term "substantially simultaneously," as used herein, is intended to mean simultaneously or approximately simultaneously and is meant to encompass variations of 15%, 10%, 5%, 1%, 0.5%, or even 0.1% of the specified time of occurrence.

The term "substantially later in time" as used herein, is intended to mean not simultaneously, and, is meant to encompass time differences of greater than 15%, 20%, 30%, or even 50% of the specified time difference, or a difference that is statistically significantly later in time.

Compositions

The present disclosure provides a composition for assessing gut function in a subject in need thereof, comprising a fluorescent challenge molecule, wherein the fluorescent challenge molecule is not substantially absorbed by a healthy gut. Additionally, a second fluorescent challenge molecule, a control molecule that may be absorbed in health and disease, and thereby serve as a normalizing determination against which the larger molecule's uptake will be measured. These compositions may be measured within a subject utilizing noninvasive techniques, and provide real time data and results.

The fluorescent challenge molecule may be a fluorescent dye. The fluorescent dyes of the present disclosure tend to have absorption, excitation, and emission wavelengths that are all within the near-infrared (NIR) or visible spectrum of about 350 nm or greater. This is beneficial for diagnostic procedures since visible and NIR light are not likely to damage tissue. In contrast, ultraviolet (UV) light that has a wavelength of less than about 350 nm can damage tissue. Light having a wavelength of about 350 nm or greater tends to penetrate into tissues thereby permitting diagnostic procedures to be conducted in tissues of interest that may not be reachable using UV wavelengths that are less than about 350 nm. Suitable fluorescent dyes include acridines, acridones, anthracenes, anthracylines, anthraquinones, azaazulenes, azo azulenes, benzenes, benzimidazoles, benzofurans, benzoindocarbocyanines, benzoindoles, benzothiophenes, carbazoles, coumarins, cyanines, dibenzofurans, dibenzothiophenes, dipyrrolo dyes, flavones, fluoresceins, imidazoles, indocarbocyanines, indocyanines, indoles, isoindoles, isoquinolines, naphthacenediones, naphthalenes, naphthoquinones, phenanthrenes, phenanthridines, phenanthridines, phenoselenazines, phenothiazines, phenoxazines, phenylxanthenes, polyfluorobenzenes, purines, pyrazines, pyrazoles, pyridines, pyrimidones, pyrroles, quinolines, quinolones, rhodamines, squaraines, tetracenes, thiophenes, triphenyl methane dyes, xanthenes, xanthones, and derivatives thereof. In certain embodiments, the fluorescent dye is a pyrazine.

The uptake of larger molecules reflects gut porosity. Thus, the fluorescent challenge molecule is relatively large. Specific embodiments include 3,6-diamino-2,5-bis{N-[(1R)-1-carboxy-2-hydroxyethyl]carbamoyl}pyrazine and 3,6-N,N'-bis(2,3-dihydroxypropyl)-2,5-pyrazinedicarboxamide.

The fluorescent challenge molecule may be a fluorescent dye conjugated to a carbohydrate. Suitable carbohydrates include large molecular weight carbohydrates such as lactulose (MW=342), sucrose (MW=342), mannitol (MW=180), and sucralose (MW=398). There is some site specificity: lactose and lactulose reflect porosity in the small bowel, sucrose reflects porosity in the stomach, and sucralose reflects porosity in the large bowel. In certain embodiments, the carbohydrate is lactulose.

The fluorescent challenge molecule may be a fluorescent dye conjugated to polyethylene glycol (PEG). Polyethylene glycol refers to oligomers and polymers with a molecular mass below 20,000 g/mol. As referred to herein, a "PEG unit" means a —$CH_2CH_2O$-unit. PEG units are typically components of highly soluble oligomers and polymers of ethylene glycol. Further, they tend to be highly biocompatible, non-immunogenic, and non-toxic.

The composition may include a second fluorescent challenge molecule, wherein the fluorescent challenge molecule is substantially absorbed by a healthy gut. The second challenge molecule may be similar to the first challenge molecule, in that it may include a fluorescent dye; however, the second molecule is designed to be absorbed by the gut. In certain embodiments, the second fluorescent challenge molecule is 3,6-diaminopyrazine-2,5-dicarboxylic acid.

The second challenge molecule may also include a fluorescent dye conjugated to a carbohydrate. Carbohydrates include smaller molecular weight carbohydrates such as D-xylose (MW=150), mannitol (MW=180), and rhamnose (MW=164). D-xylose, a pentose, is the most established of the sugar challenge substances. Humans do not have D-xylose isomerase so the intact molecule is cleared without digestion or degradation, and the mechanism of clearance is glomerular filtration. In certain embodiments, the carbohydrate is mannitol.

For compositions comprising a second fluorescent challenge molecule, the second molecule may possess different photophysical properties from the first challenge molecule. Thus, the two molecules display different absorption and emission wavelengths, and allow real-time measurement of uptake and permeability in the gut. In certain embodiments, the second fluorescent challenge molecule fluoresces at a wavelength different from the first fluorescent challenge molecule.

Methods

The present disclosure provides new methods for assessing gut function in a subject in need thereof, including the steps of: administering an effective amount of a fluorescent challenge molecule described herein into the subject's gut; irradiating the composition absorbed by the subject's gut with non-ionizing radiation, wherein the radiation causes the composition to fluoresce; detecting the fluorescence of the composition; and assessing gut function in the subject based on the detected fluorescence and its kinetics of appearance in the blood.

In certain embodiments, the composition is administered orally.

In certain embodiments, the non-ionizing radiation has a wavelength of at least 350 nm.

In certain embodiments, the composition absorbed by the subject's gut is irradiated and detected in the subject's skin, blood, urine, or fascia. In certain embodiments, the composition absorbed by the subject's gut is irradiated and detected transcutaneously. In certain embodiments, the detected fluorescence of the fluorescent challenge molecules is measured over time.

Provided is a method for assessing gut function in a subject in need thereof, comprising the steps of: administering an effective amount of a composition comprising two fluorescent challenge molecules—a fluorescent challenge molecule that is not substantially absorbed by a healthy gut, and a second fluorescent challenge molecule is substantially absorbed by a healthy gut—into the subject's gut; irradiating the composition absorbed by the subject's gut with non-ionizing radiation, wherein the radiation causes the composition to fluoresce; detecting the fluorescence of each fluorescent challenge molecule in the composition; and assessing gut function in the subject based on the detected fluorescence. Gut function is assessed by comparing the detected fluorescence of the fluorescent challenge molecule that is not substantially absorbed by a healthy gut to the fluorescent challenge molecule that is substantially absorbed by a healthy gut. The two fluorescent challenge molecules may possess different photophysical properties allowing for the simultaneous measurement of the fluorescence the two molecules.

In certain embodiments, the composition is administered orally. In certain embodiments, the non-ionizing radiation has a wavelength of at least 350 nm.

In certain embodiments, the composition absorbed by the subject's gut is irradiated and detected in the subject's skin, blood, urine, or fascia. In certain embodiments, the composition absorbed by the subject's gut is irradiated and detected transcutaneously. In certain embodiments, the detected fluorescence of the fluorescent challenge molecules is measured over time.

Also provided is a method of assessing the location of a disease or an injury in a subject's gut, comprising the steps of: administering an effective amount of a composition containing a fluorescent challenge molecule that is not substantially absorbed by a healthy gut, and a second fluorescent challenge molecule is substantially absorbed by a healthy gut into the subject's gut; irradiating the composition absorbed by the subject's gut with non-ionizing radiation, wherein the radiation causes the composition to fluoresce; detecting the fluorescence of each fluorescent challenge molecule in the composition over time; and assessing the location of disease or injury in the subject's gut, based on the time period between the detected fluorescence of each fluorescent challenge molecule and administration. Again, the two fluorescent challenge molecules may possess different photophysical properties allowing for the simultaneous measurement of the fluorescence the two molecules.

In certain embodiments, the composition is administered orally. In certain embodiments, the non-ionizing radiation has a wavelength of at least 350 nm.

In certain embodiments, the composition absorbed by the subject's gut is irradiated and detected in the subject's skin, blood, urine, or fascia. In certain embodiments, the composition absorbed by the subject's gut is irradiated and detected transcutaneously.

In certain embodiments, the detected fluorescence of the challenge molecule that is not substantially absorbed by a healthy gut occurs before or substantially simultaneously as compared the detected fluorescence of the challenge molecule that is substantially absorbed by a healthy gut— indicating that the disease or injury is located in the proximal portion of the gut. In particular embodiments, this may indicate the subject is suffering from Celiac disease.

In certain embodiments, the detected fluorescence of the challenge molecule that is not substantially absorbed by a healthy gut occurs substantially later in time as compared the detected fluorescence of the challenge molecule that is substantially absorbed by a healthy gut—indicating that the disease or injury is located in the distal portion of the gut. In particular embodiments, this may indicate the subject is suffering from ulcerative colitis.

Also provided is a method of assessing the size of the openings within a subject's gut, comprising the steps of: administering an effective amount of a composition comprising at least one fluorescent challenge molecule, wherein each fluorescent challenge molecule has a different size, and is absorbed by a healthy gut to a different degree into the subject's gut; irradiating the composition absorbed by the subject's gut with non-ionizing radiation, wherein the radiation causes the composition to fluoresce; detecting the fluorescence of each fluorescent challenge molecule in the composition; and assessing the size of the openings within the subject's gut, based on the size of each fluorescent challenge molecule.

In certain embodiments, the size of the challenge molecules absorbed by the subject's gut indicates the minimum size of the openings within the subject's gut.

Kits

The present disclosure provides a kit for assessing gut function in a subject in need thereof, comprising: a composition comprising a fluorescent challenge molecule as described herein, wherein the fluorescent challenge molecule is not substantially absorbed by a healthy gut, and written instructions for assessing gut function in the subject, comprising the steps of: administering an effective amount of a composition of a. into the subject's gut; irradiating the composition absorbed by the subject's gut with non-ionizing radiation, wherein the radiation causes the composition to fluoresce; detecting the fluorescence of the composition; and assessing gut function in the subject based on the detected fluorescence.

In certain embodiments, the instructions include a step for administering the composition orally.

In certain embodiments, the instructions include a step for irradiating the composition with the non-ionizing radiation having a wavelength of at least 350 nm.

In certain embodiments, the instructions include a step for irradiating and detecting the composition absorbed by the subject's gut within the subject's skin, blood, urine, or fascia.

In certain embodiments, the instructions include a step for irradiating and detecting the composition transcutaneously.

In certain embodiments, the instructions include a step for detecting and measuring fluorescence of the fluorescent challenge molecules over time.

Provided is a kit for assessing gut function in a subject in need thereof, comprising: a composition comprising two fluorescent challenge molecules—a fluorescent challenge molecule that is not substantially absorbed by a healthy gut, and a second fluorescent challenge molecule is substantially absorbed by a healthy gut into the subject's gut, and written instructions for assessing gut function in the subject, comprising the steps of: administering an effective amount of the composition comprising two fluorescent challenge molecules into the subject's gut; irradiating the composition absorbed by the subject's gut with non-ionizing radiation, wherein the radiation causes the composition to fluoresce; detecting the fluorescence of each fluorescent challenge molecule in the composition; and assessing gut function in the subject based on the detected fluorescence.

In certain embodiments, the instructions include a step for administering the composition orally.

In certain embodiments, the instructions include a step for irradiating the composition with the non-ionizing radiation having a wavelength of at least 350 nm.

In certain embodiments, the instructions include a step for irradiating and detecting the composition absorbed by the subject's gut within the subject's skin, blood, urine, or fascia.

In certain embodiments, the instructions include a step for irradiating and detecting the composition transcutaneously.

In certain embodiments, the instructions include a step for detecting and measuring fluorescence of the fluorescent challenge molecules over time.

In certain embodiments, the instructions include a step for comparing the detected fluorescence of the fluorescent challenge molecule that is not substantially absorbed by a healthy gut to the fluorescent challenge molecule that is substantially absorbed by a healthy gut.

Also provided is a kit for assessing gut function in a subject in need thereof, comprising: a composition comprising two fluorescent challenge molecules—a fluorescent challenge molecule that is not substantially absorbed by a healthy gut, and a second fluorescent challenge molecule is substantially absorbed by a healthy gut into the subject's gut, and written instructions for assessing gut function in the subject, comprising the steps of: administering an effective amount of the composition into the subject's gut; irradiating the composition absorbed by the subject's gut with non-ionizing radiation, wherein the radiation causes the composition to fluoresce; detecting the fluorescence of each fluorescent challenge molecule in the composition over time; and assessing the location of disease or injury in the subject's gut, based on the time period between the detected fluorescence of each fluorescent challenge molecule and administration.

In certain embodiments, the instructions include a step for administering the composition orally.

In certain embodiments, the instructions include a step for irradiating the composition with the non-ionizing radiation having a wavelength of at least 350 nm.

In certain embodiments, the instructions include a step for irradiating and detecting the composition absorbed by the subject's gut within the subject's skin, blood, urine, or fascia.

In certain embodiments, the instructions include a step for irradiating and detecting the composition transcutaneously.

In certain embodiments, the instructions include a step for detecting and measuring fluorescence of the fluorescent challenge molecules over time.

Formulation

The compositions of the present disclosure may be administered orally, including by swallowing, so that the compound enters the gastrointestinal tract.

Suitable compositions for oral administration include solid formulations such as tablets, lozenges and capsules, which can contain liquids, gels, or powders. Liquid formulations can include solutions, syrups and suspensions, which can be used in soft or hard capsules. Such formulations may include a pharmaceutically acceptable carrier, for example, water, ethanol, polyethylene glycol, cellulose, phosphate-buffered saline (PBS), or an oil. The formulation may also include one or more emulsifying agents and/or suspending agents. Preparation of pharmaceutically acceptable formulations can be accomplished according to methods known in the art.

Dosage

Compositions of the present disclosure may be administered in a single dose or in multiple doses to achieve an effective diagnostic objective. After administration, the composition is allowed time to move into the gut, and the selected target site is exposed to light with a sufficient power and intensity to detect light emanating from the compound within the patient's body to provide information that may be utilized by a healthcare provider (e.g., in making a diagnosis). Doses may vary widely depending upon, for example, the particular integrated photoactive agent employed, the areas (e.g., organs or tissues) to be examined, the equipment employed in the clinical procedure, the efficacy of the treatment achieved, and/or the like. For example, the dosage of the compound may vary from about 0.1 mg/kg body weight to about 500 mg/kg body weight in some embodiments. In other embodiments, the dosage of the compound may vary from about 0.5 to about 2 mg/kg body weight.

Detection and Measurement

After administration, the composition is allowed time to move into the gut, and the selected target site is exposed to light with a sufficient power and intensity to detect light emanating from the compound within the patient's body to provide information that may be utilized by a healthcare provider (e.g., in making a diagnosis). Detection of the composition may be achieved by optical fluorescence, absorbance, and/or light scattering methods using invasive and/or non-invasive probes such as endoscopes, catheters, ear clips, hand bands, headbands, surface coils, finger probes, and/or the like. Imaging can be achieved using planar imaging, optical tomography, optical coherence tomography, endoscopy, photoacoustic technology, sonofluorescence technology, light scattering technology, laser assisted guided surgery (LAGS), confocal microscopy, dynamic organ function monitoring, and/or light scattering devices.

Detection and measurement of the fluorescence signal may be determined as a function of time after delivery of the compositions disclosed herein. Comparison of peak fluorescence signal times may provide information regarding the location of any injuries or disease within the gut.

In order that the disclosure described herein may be more fully understood, the following examples are set forth. It should be understood that these examples are for illustrative purposes only and are not to be construed as limiting this disclosure in any manner.

EXAMPLES

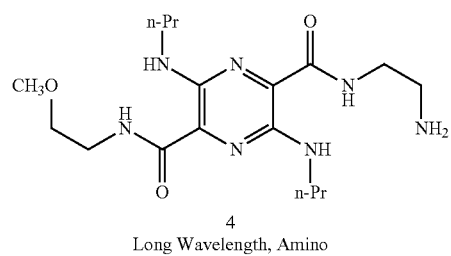

4
Long Wavelength, Amino

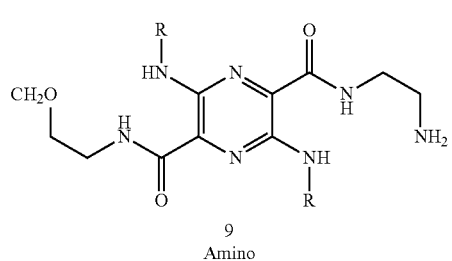

13
Amino

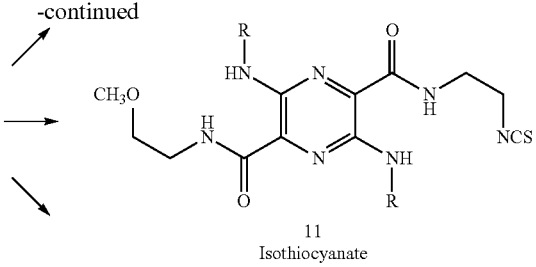

14
Isothiocyanate

-continued

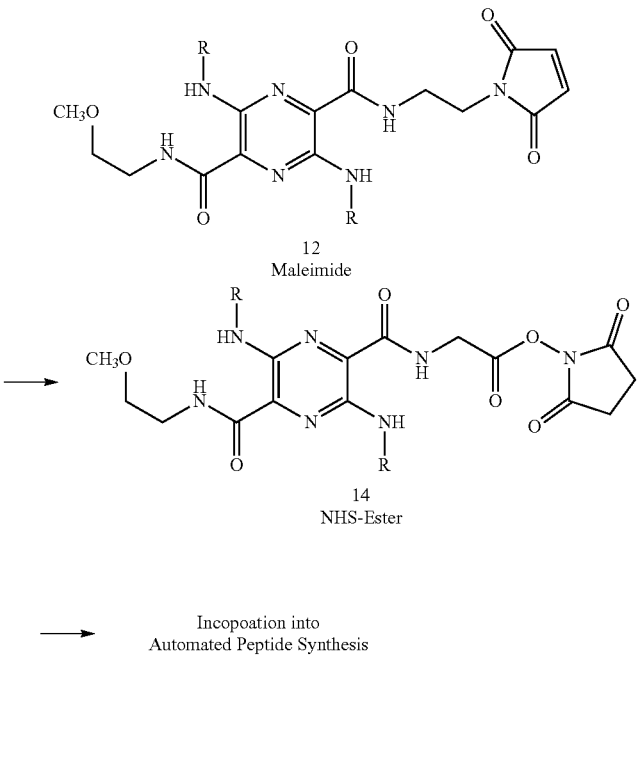

12
Maleimide

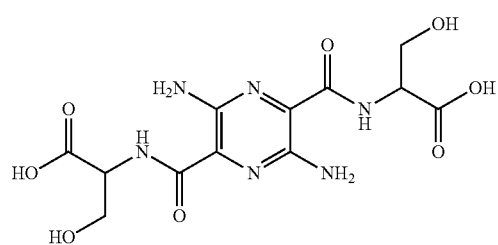 [SMILES: Nc1nc(C(=O)NC(CO)C(=O)O)c(N)nc1C(=O)NC(CO)C(=O)O]

13
Carbonyl

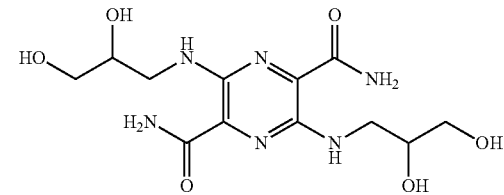 [SMILES: NC(=O)c1nc(NCC(O)CO)c(C(N)=O)nc1NCC(O)CO]

14
NHS-Ester

Incopoation into
Automated Peptide Synthesis

15
Bifunctional Pyrazine, Amino-Carbonyl

Figure 3:
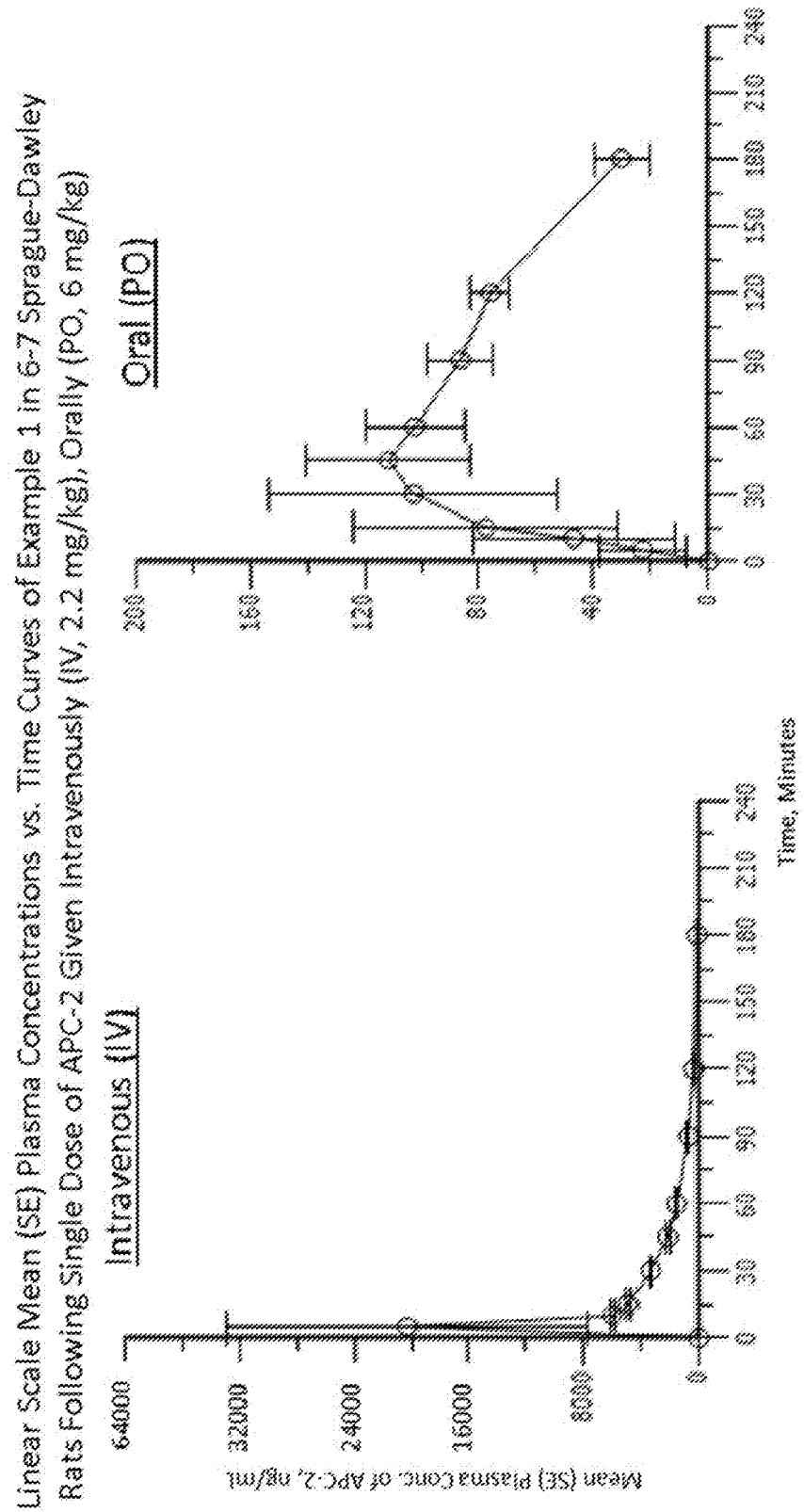
FIG. 3 shows Plasma Concentrations vs. Time Curves of Example 1 in Sprague-Dawley Rats Following Single Dose of Example Compound 1 given Intravenously and Orally.

Example 1: 3,6-diamino-2,5-bis{N-[(1R)-1-carboxy-2-hydroxyethyl]carbamoyl}pyrazine Example 2: 3,6-N,N'-bis(2,3-dihydroxypropyl)-2,5-pyrazinedicarboxamide This fluorescent challenge molecule exhibits light absorption and emission maxima at 445 nm and 560 nm, respectively. FIG. 3 shows the IV and oral clearance of Example 1, which indicates that there is very little oral bioavailability for this relatively high molecular weight (372 g/mol) compound in rats having "normal" gut function. Example 1 may be categorized as fluorescent challenge molecule is not substantially absorbed by a healthy gut.

Figure 5:
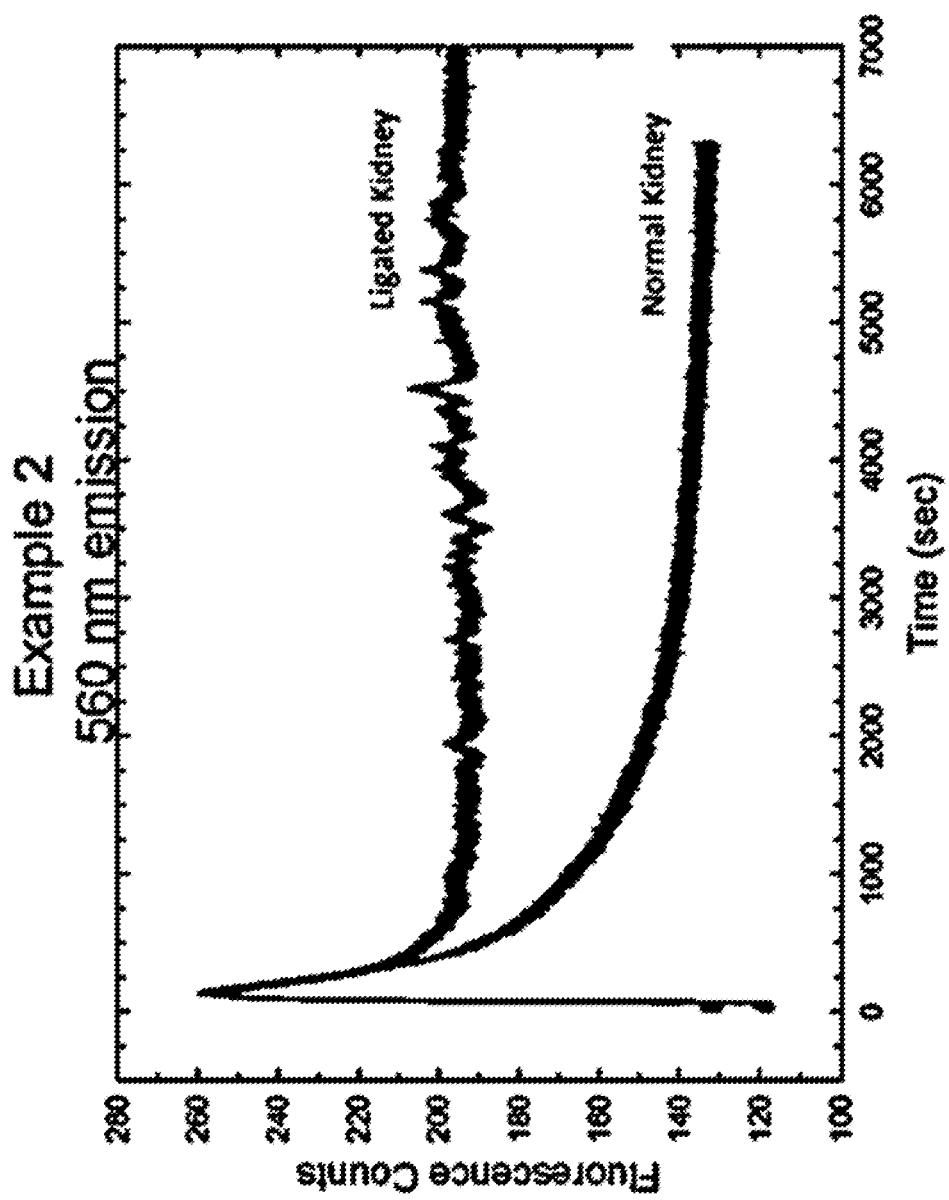
FIG. 5 shows Example Compound 3 clears from the body via the renal system.

This fluorescent challenge molecule exhibits light absorption and emission maxima at 486 nm and 600 nm, respectively. FIG. 5 shows the molecule's emission spectra. Example 2 may be categorized as fluorescent challenge molecule is not substantially absorbed by a healthy gut as the molecular weight is relatively high (344 g/mol).

Example 3: 3,6-diaminopyrazine-2,5-dicarboxylic Acid

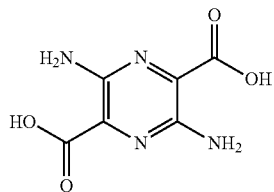 [SMILES: Nc1nc(C(=O)O)c(N)nc1C(=O)O]

Figure 4:
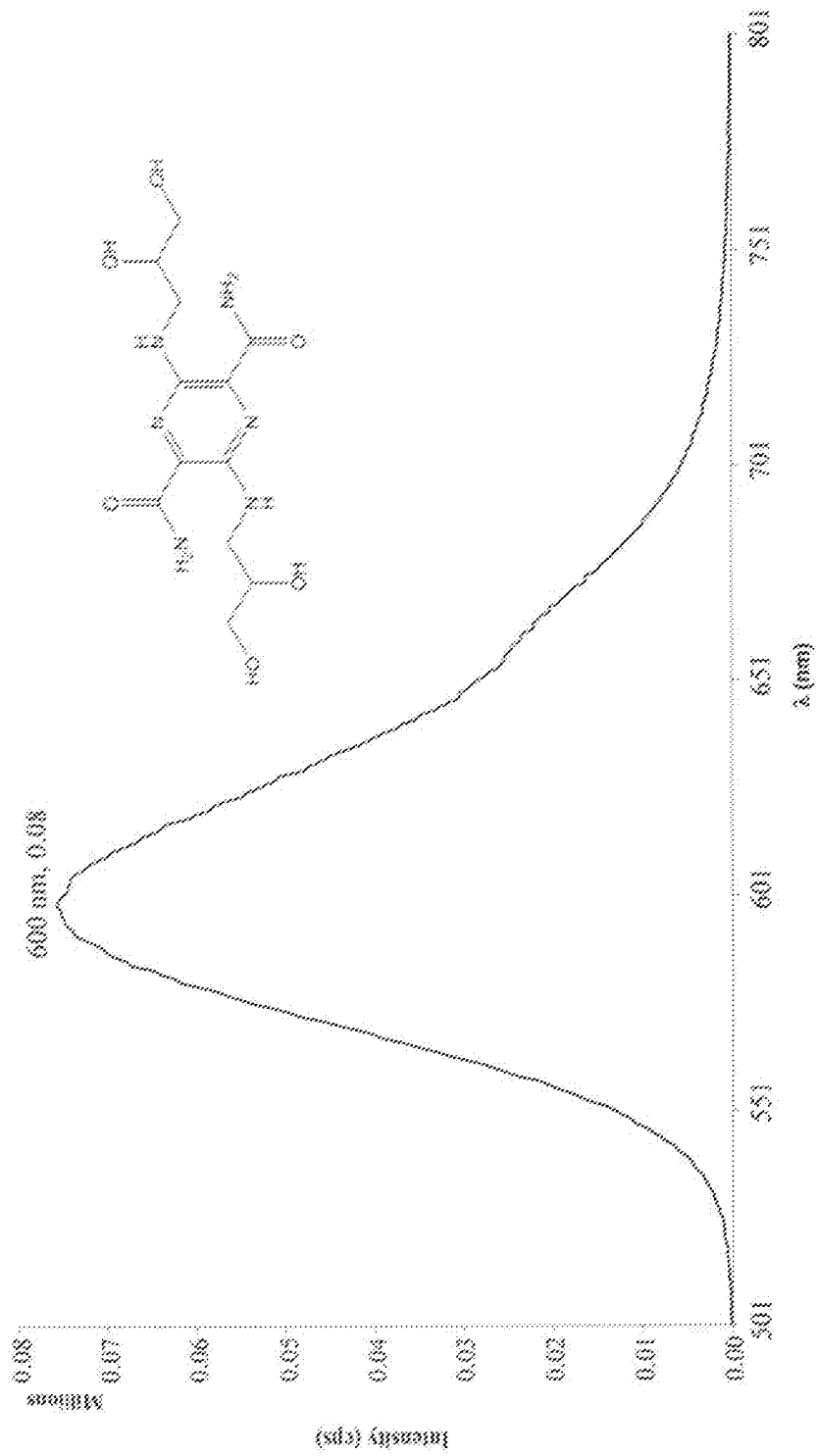
FIG. 4 shows the emission spectra of Example Compound 2.

The graph shown in FIG. 4 shows the low molecular weight compound clears from the body by the renal system. When the kidneys are ligated, the compound has no excretion pathway and the fluorescence signal stays elevated because it does not clear. This fluorescent challenge molecule exhibits light absorption and emission maxima at 396 nm and 536 nm, respectively. Example 3 may be categorized as fluorescent challenge molecule that is substantially absorbed by a healthy gut as the molecular weight is relatively low (198 g/mol).

Example 4: Assessing Gut Function

An exemplary procedure for assessing gut function is as follows: a composition containing a fluorescent challenge molecule that is not substantially absorbed by a healthy gut is administered to a subject. The challenge molecule passes into the subject's gut, and if the gut is injured or diseased in such a way that increases the gut's permeability, the challenge molecule will be absorbed from the gut into the subject's bloodstream. While in the blood stream, the fluorescent challenge molecule may be irradiated with non-ionizing radiation, wherein the radiation causes the composition to fluoresce. The fluorescence of any absorbed challenge molecule may be detected in the bloodstream; and the gut function may be assessed based on the detected fluorescence. The appearance of the fluorescent challenge molecule in the bloodstream indicates the gut has increased permeability.

Another exemplary procedure begins with the administration of a composition comprising two fluorescent challenge molecules, wherein the first fluorescent challenge molecule is not substantially absorbed by a healthy gut, and the second fluorescent challenge molecule is substantially absorbed by a healthy gut. The second challenge molecule that is substantially absorbed by a healthy gut will pass into the subject's gut, and if the gut is injured or diseased in such a way that increases the gut's permeability, the first challenge molecule will be absorbed from the gut into the subject's bloodstream. While in the blood stream, the fluorescent challenge molecules may be irradiated with non-ionizing radiation, wherein the radiation causes the fluorescent challenge molecules present to fluoresce. The fluorescence of each absorbed challenge molecule may be detected in the bloodstream; and the gut function may be assessed by comparing the detected fluorescence of the fluorescent challenge molecule that is not substantially absorbed by a healthy gut to the fluorescent challenge molecule that is substantially absorbed by a healthy gut. The second challenge molecule that is substantially absorbed by a healthy gut functions as a control, and minimizes effects of digestion kinetics on the results.

The ratio of the first fluorescent challenge molecule that is not substantially absorbed by a healthy gut, and the second fluorescent challenge molecule that is substantially absorbed by a healthy gut is used to assess gut function. A high ratio indicates the gut is highly permeable, and a low ratio indicates low permeability.

Yet another exemplary procedure may be performed as described above, but in addition, the fluorescence of each absorbed challenge molecule may be detected in the bloodstream over time; and the location of disease or injury in the subject's gut may be determined based on the time between the detected fluorescence of each fluorescent challenge molecule and administration. If the detected fluorescence of the challenge molecule that is not substantially absorbed by a healthy gut occurs before or nearly the same time as compared the detected fluorescence of the challenge molecule that is substantially absorbed by a healthy gut indicates that the disease or injury is located in the proximal portion of the gut. If the detected fluorescence of the challenge molecule that is not substantially absorbed by a healthy gut occurs at nearly the same time as compared the detected fluorescence of the challenge molecule that is substantially absorbed by a healthy gut indicates that the disease or injury is located in the proximal portion of the gut.

The time difference occurs as the composition moves through the gut. If the gut is permeable at the proximal portion, or throughout the gut, both challenge molecules should appear at the same time. If only the distal portion is permeable, the challenge molecule that is not substantially absorbed by a healthy gut should be detected later than the challenge molecule that is substantially absorbed by a healthy gut.

The graph shown in FIG. 4 shows the low molecular weight compound clears from the body by the renal system. When the kidneys are ligated, the compound has no excretion pathway and the fluorescence signal stays elevated because it does not clear. This fluorescent challenge molecule exhibits light absorption and emission maxima at 396 nm and 536 nm, respectively. Example 3 may be categorized as fluorescent challenge molecule that is substantially absorbed by a healthy gut as the molecular weight is relatively low (198 g/mol).

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

What is claimed is:

1. A method for assessing gut function in a subject in need thereof, comprising the steps of:
   a. administering an effective amount of a composition for assessing gut function, the composition comprising a fluorescent challenge molecule, wherein the fluorescent challenge molecule is not substantially absorbed by a healthy gut;
   b. irradiating the fluorescent challenge molecule absorbed by the subject's gut with non-ionizing radiation, wherein the radiation causes the fluorescent challenge molecule to fluoresce;

c. detecting the fluorescence of the fluorescent challenge molecule; and d. assessing gut function in the subject based on the detected fluorescence, wherein the subject is a human, wherein the fluorescent challenge molecule is a fluorescent dye selected from the group consisting of 3,6-diamino-2,5-bis{N-[(1R)-1-carboxy-2-hydroxyethyl]carbamoyl}pyrazine and 3,6-N,N'-bis(2,3-dihydroxypropyl)-2,5-pyrazinedicarboxamide, wherein the non-ionizing radiation has a wavelength of at least 350 nm, and wherein the fluorescent challenge molecule absorbed by the subject's gut is irradiated and detected in the subject's skin, blood, urine, or fascia.

2. The method of claim 1, wherein the composition is administered orally.

3. The method of claim 1, wherein the fluorescent challenge molecule absorbed by the subject's gut is irradiated and detected transcutaneously.

4. The method of claim 1, wherein the detected fluorescence of the fluorescent challenge molecules is measured over time.

5. The method according to claim 1, wherein the composition for assessing gut function further comprises at least one pharmaceutically acceptable carrier, pharmaceutically acceptable emulsifying agent, pharmaceutically acceptable suspending agent or any combination thereof.

6. The method according to claim 1, wherein the fluorescent challenge molecule is cleared from the body of the subject only by glomerular filtration.

7. The method of claim 1, wherein the fluorescent challenge molecule absorbed by the subject's gut is irradiated and detected in the urine of the subject.

8. The method of claim 1, wherein the method is noninvasive for the subject.

9. The method of claim 1, wherein the fluorescent challenge molecule is 3,6-diamino-2,5-bis{N-[(1R)-1-carboxy-2-hydroxyethyl]carbamoyl}pyrazine.

* * * * *

UNITED STATES PATENT AND TRADEMARK OFFICE
CERTIFICATE OF CORRECTION

PATENT NO. : 11,285,223 B2
APPLICATION NO. : 16/200311
DATED : March 29, 2022
INVENTOR(S) : Dorshow et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 119 days.

Signed and Sealed this
Twenty-ninth Day of November, 2022

Katherine Kelly Vidal
*Director of the United States Patent and Trademark Office*